US012672808B2

(12) United States Patent
Yoo et al.

(10) Patent No.: US 12,672,808 B2
(45) Date of Patent: Jul. 7, 2026

(54) METHOD, SYSTEM, AND COMPUTER-READABLE MEDIUM FOR PROVIDING DEPRESSION PRELIMINARY DIAGNOSIS INFORMATION BY USING MACHINE LEARNING MODEL

(71) Applicant: GENESIS LAB, INC., Seoul (KR)

(72) Inventors: Daehun Yoo, Seoul (KR); Youngbok Lee, Seoul (KR); Junhong Kim, Seoul (KR)

(*) Notice: Subject to any disclaimer, the term of this patent is extended or adjusted under 35 U.S.C. 154(b) by 303 days.

(21) Appl. No.: 18/258,865

(22) PCT Filed: Nov. 25, 2021

(86) PCT No.: PCT/KR2021/017512
§ 371 (c)(1),
(2) Date: Jun. 22, 2023

(87) PCT Pub. No.: WO2022/149720
PCT Pub. Date: Jul. 14, 2022

(65) Prior Publication Data
US 2024/0041371 A1     Feb. 8, 2024

(30) Foreign Application Priority Data

May 1, 2021     (KR) ......................... 10-2021-0000837

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/4803* (2013.01); *A61B 5/7264* (2013.01); *A61B 5/742* (2013.01); *G16H 40/67* (2018.01); *G16H 50/20* (2018.01)

(58) Field of Classification Search
CPC ................................ A61B 5/165; G16H 50/20
See application file for complete search history.

(56) References Cited

U.S. PATENT DOCUMENTS

2019/0355474 A1     11/2019  Mellem et al.
2019/0385711 A1*    12/2019  Shriberg ................ G16H 15/00
2022/0130427 A1*     4/2022  Allibhai .................. G10L 25/57

FOREIGN PATENT DOCUMENTS

KR     10-2017-0081859     7/2017
KR     10-2020-0092460     8/2020
(Continued)

OTHER PUBLICATIONS

"Office Action for Korea Patent Application No. 10-2021-0000837, mailed Aug. 23, 2022.".
(Continued)

*Primary Examiner* — Thomas J Hong
(74) *Attorney, Agent, or Firm* — Youngil Lee

(57) ABSTRACT
The present invention relates to a method, a system, and a computer-readable medium for providing depression preliminary diagnosis information by using a machine learning model, in which a result of analysis on depression with respect to an answer video performed by a person to be evaluated and supporting information therefor are provided to medical staff, users, counselors and the like through a special user interface, so as to more efficiently determine the depression.

12 Claims, 11 Drawing Sheets

(51) Int. Cl.
    *G16H 40/67*          (2018.01)
    *G16H 50/20*          (2018.01)

(56)            References Cited

FOREIGN PATENT DOCUMENTS

| KR | 10-2020-0092512 | 8/2020 |
| KR | 10-2020-0145299 | 12/2020 |

OTHER PUBLICATIONS

"PCT International Search Report and Written Opinion for International Application No. PCT/KR2021/017512, Date of Mailing: Mar. 3, 2022".

\* cited by examiner

FIG. 1

METHOD, SYSTEM, AND COMPUTER-READABLE MEDIUM FOR PROVIDING DEPRESSION PRELIMINARY DIAGNOSIS INFORMATION BY USING MACHINE LEARNING MODEL

TECHNICAL FIELD

The present invention relates to a method, a system, and a computer-readable medium for providing depression preliminary diagnosis information by using a machine learning model, and more particularly, to a method, a system, and a computer-readable medium for providing depression preliminary diagnosis information by using a machine learning model, in which a result of analysis on depression with respect to an answer video performed by a person to be evaluated and supporting information therefor are provided to medical staff, users, counselors and the like through a special user interface, so as to more efficiently determine the depression.

BACKGROUND ART

Recent, there is a need for suicide prevention measures with a more active form as clear red flags have been revealed on the mental health of the people due to impact of COVID-19. Currently, a patient self-diagnosed as being in the early stages of mental illness visits a psychiatric hospital and receive a diagnosis. However, it is difficult for an ordinary person to easily visit a hospital and receive diagnosis and consultation.

Particularly, suicide rates among people in their 20s and 30s, students, and women are recently increasing at a considerable rate. However, since the above young ages have a psychological reluctance to treat psychiatric diseases or a reluctance to have a history of psychiatric disease treatment left in their history, it is difficult to easily visit a psychiatric hospital.

In addition, it is necessary for counselors to know the state and degree of depression in order to respond for treating the depression. However, the counselors mostly rely on questionnaires such as the PHQ-9. The questionnaire has a limitation in diagnosis because it is not guaranteed that the patient accurately fills out a state of the patient.

In addition, Related Patent 1 (Korean Patent Registration No. 10-2175490) discloses the technology in which a conversational interface is provided to a user through an artificial intelligence speaker, one of pre-set corpus corresponding to each of questionnaires for measuring depression is selected and provided as conversation content to the user according to the user's response to the provided conversation, and all responses to the questionnaires for measuring depression are received and analyzed to measure the depression.

In addition, Related Patent 2 (Korean Patent Publication No. 10-2020-0042373) discloses the technology configured such that electroencephalogram data is obtained, a refined composite multi-scale permutation entropy (RCMPE) index is detected based on the electroencephalogram data, and electroencephalogram variability for the electroencephalogram data is detected by using the refined composite multiscale permutation entropy index.

However, in Related Patent 1, convenience may be provided to users, but depression cannot be accurately diagnosed simply by voice information only. In Related Patent 2, since equipment for the corresponding diagnosis are required for most users, the users may feel uncomfortable and user convenience may be reduced.

In addition, since only the doctors can accurately diagnose depression finally and prescriptions for the diagnosis and advice to patients are ultimately wanted by people suffering from mental illness such as depression, the approaches such as Related Patents 1 and 2 without activities of a professional doctor basically have limitations.

In addition, as the remote technology arises recently, psychiatric doctors or counselors can also counsel and diagnose patients through video communication. However, for the above remote technology, since doctors and patients are required to perform counseling and diagnoses at the same time, it takes the same amount of time after all from a doctor's point of view, and further, convenience of treatment is reduced. For these reasons, the remote technology has not been actively adopted.

In addition, as the society rapidly changes recently, the age group affected by depression has been broadening, and the number of people who need various counseling and diagnoses has been rapidly increasing. However, since the number of psychiatrists is limited, it is difficult to diagnose based on sufficient analysis in actual treatment or counseling.

DISCLOSURE

Technical Problem

An object of the present invention is to provide a method, a system, and a computer-readable medium for providing depression preliminary diagnosis information by using a machine learning model, in which a result of analysis on depression with respect to an answer video performed by a person to be evaluated and supporting information therefor are provided to medical staff, users, counselors and the like through a special user interface, so as to more efficiently determine the depression.

Technical Solution

In order to solve the above technical problem, one embodiment of the present invention provides a method for providing depression preliminary diagnosis information by using a machine learning model performed on a computing device having at least one processor and at least one memory, which includes: a diagnosing step of deriving depression preliminary diagnosis information by using a machine-learned model for at least one answer video; and a providing step of providing the depression preliminary diagnosis information to a user, wherein a first display screen displayed by the providing step includes: an answer video layer for displaying the answer video; and a script layer for displaying question information related to the answer video and answer text information extracted from the answer video, wherein a video time point of the answer video layer may be changed to a time point corresponding to a position of a script part selected according to an input by the user in the script layer.

In some embodiments of the invention, the first display screen may include: a depression graph layer for displaying a degree of depression diagnosed according to a time axis, wherein a video time point of the answer video layer may be changed to a time point corresponding to a position on the time axis selected according to an input by the user in the depression graph layer.

In some embodiments of the invention, in the diagnosing step, the depression preliminary diagnosis information may be derived by using the machine-learned model from the answer video, based on multiple words extracted from text of a voice, multiple image frames corresponding to the words, respectively, and multiple pieces of voice information corresponding to the words, respectively.

In some embodiments of the invention, the diagnosing step may include: a first step of extracting multiple words, multiple image frames, and multiple pieces of voice information extracted from text of a voice from the answer video; a second step of deriving multiple pieces of first feature information, multiple pieces of second feature information, and multiple pieces of third feature information from the words, the image frames and the pieces of voice information by using each detailed machine learning model or algorithm; and a third step of deriving derived information including a degree of depression by using an artificial neural network considering sequence data from the pieces of first feature information, the pieces of second feature information, and the pieces of third feature information.

In some embodiments of the invention, in the diagnosing step, the depression preliminary diagnosis information may be derived by using the machine-learned model, based on at least two pieces of information among multiple words, multiple image frames, and voice information extracted from text of a voice extracted from the answer video.

In some embodiments of the invention, the artificial neural network considering the sequence data may correspond to a recurrent neural network or a transformer-based machine learning model based on an attention mechanism, and the first feature information, the second feature information, and the third feature information corresponding to each of the words may be input, in a merged form, to the recurrent neural network or the transformer-based machine learning model.

In some embodiments of the invention, the part of the answer text displayed on the script layer may be displayed with change in at least one of highlight, font, size, color, and underline according to at least one of a degree of depression and a type of depression in the depression preliminary diagnosis information corresponding to the corresponding part of the answer text.

In some embodiments of the invention, the part of the answer text displayed with the change in at least one of the highlight, font, size, color, and underline may correspond to a state in which the degree of depression of the depression preliminary diagnosis information corresponding to the part of the answer text is a predetermined reference or more, and a video time point of the answer video layer may be changed to a time point corresponding to a position of the part of the answer text when the user selects the part of the answer text displayed with the change in at least one of the highlight, font, size, color, and underline.

In some embodiments of the invention, the depression graph layer may include: a first reference display element for indicating that a degree of depression exceeds a predetermined first reference or indicating a detailed type of the depression.

In some embodiments of the invention, the first display screen may further include a scroll layer for displaying scroll information of the script layer, in which the scroll layer may display an information display element at each time point displayed according to at least one of the degree of depression and the type of depression in the depression preliminary diagnosis information, and the time point may be shifted to a position of answer text corresponding to the selected information display element in the script layer when the user selects the information display element.

In some embodiments of the invention, a second display screen displayed by the providing step may include: an answer video layer for displaying the answer video; and a summary script layer for displaying summary answer text information extracted from the answer video, in which the summary answer text information may include at least one part of the answer text in which the degree of depression in the depression preliminary diagnosis information corresponding to the part of the answer text is the predetermined reference or more, and a video time point of the answer video layer may be changed to a time point corresponding to a position of a script part selected according to an input by the user in the summary script layer.

In some embodiments of the invention, the second display screen may further include: at least one selection input element corresponding to each of the summary answer text information, in which a part of an answer video corresponding to a part of the selection input element or the summary answer text information selected according to an input of the user may be played.

In order to solve the above technical problem, one embodiment of the present invention provides a device for providing depression preliminary diagnosis information by using a machine learning model implemented as a computing device having at least one processor and at least one memory, which includes: a diagnosing unit for deriving depression preliminary diagnosis information by using a machine-learned model for at least one answer video; and a providing unit for providing the depression preliminary diagnosis information to a user, wherein a first display screen displayed by the providing step includes: an answer video layer for displaying the answer video; and a script layer for displaying question information related to the answer video and answer text information extracted from the answer video, in which a video time point of the answer video layer may be changed to a time point corresponding to a position of a script part selected according to an input by the user in the script layer.

In order to solve the above technical problem, one embodiment of the present invention provides a computer-readable medium a computer-readable medium for implementing a method for providing depression preliminary diagnosis information by using a machine learning model performed on a computing device having at least one processor and at least one memory, which includes: a diagnosing step of deriving depression preliminary diagnosis information by using a machine-learned model for at least one answer video; and a providing step of providing the depression preliminary diagnosis information to a user, wherein a first display screen displayed by the providing step includes: an answer video layer for displaying the answer video; and a script layer for displaying question information related to the answer video and answer text information extracted from the answer video, in which a video time point of the answer video layer may be changed to a time point corresponding to a position of a script part selected according to an input by the user in the script layer.

Advantageous Effects

According to one embodiment of the present invention, a method, a system, and a computer-readable medium for providing depression preliminary diagnosis information by using a machine learning model can be provided in which a result of analysis on depression with respect to an answer video performed by a person to be evaluated and supporting information therefor can be provided to medical staff through a special user interface, so as to enable the medical staff to more efficiently determine the depression.

According to one embodiment of the present invention, many users in their 20s and 30s can also receive diagnoses of their depression without feeling uncomfortable.

According to one embodiment of the present invention, a large number of people can be diagnosed on whether depression is present through a kind of telemedicine concept, and the diagnosis can be performed at separate times between patients and doctors rather than performed in real time after each doctor precisely sets the time with the patient or user.

According to one embodiment of the present invention, the medical staff can quickly check only the important parts selected by the machine learning model without playing the entire video by the medical staff.

According to one embodiment of the present invention, the parts determined as important by the machine learning model are automatically extracted, so that the videos can be checked in an efficient user interface.

In one embodiment of the present invention, voice features, facial expressions, and text are entirely determined in a multi-modal manner, so that a comprehensive determination on symptoms of depression can be provided.

In one embodiment of the present invention, information on the determination basis or explanation of the machine learning model is provided to the medical staff, rather than simply providing determination results of the machine learning model, so that the medical staff can quickly determine whether to accept the opinion.

DESCRIPTION OF DRAWINGS

FIG. 1 schematically show overall steps performed in a system for providing depression preliminary diagnosis information according to one embodiment of the present invention.

BEST MODE

Mode for Invention

Figure 2:
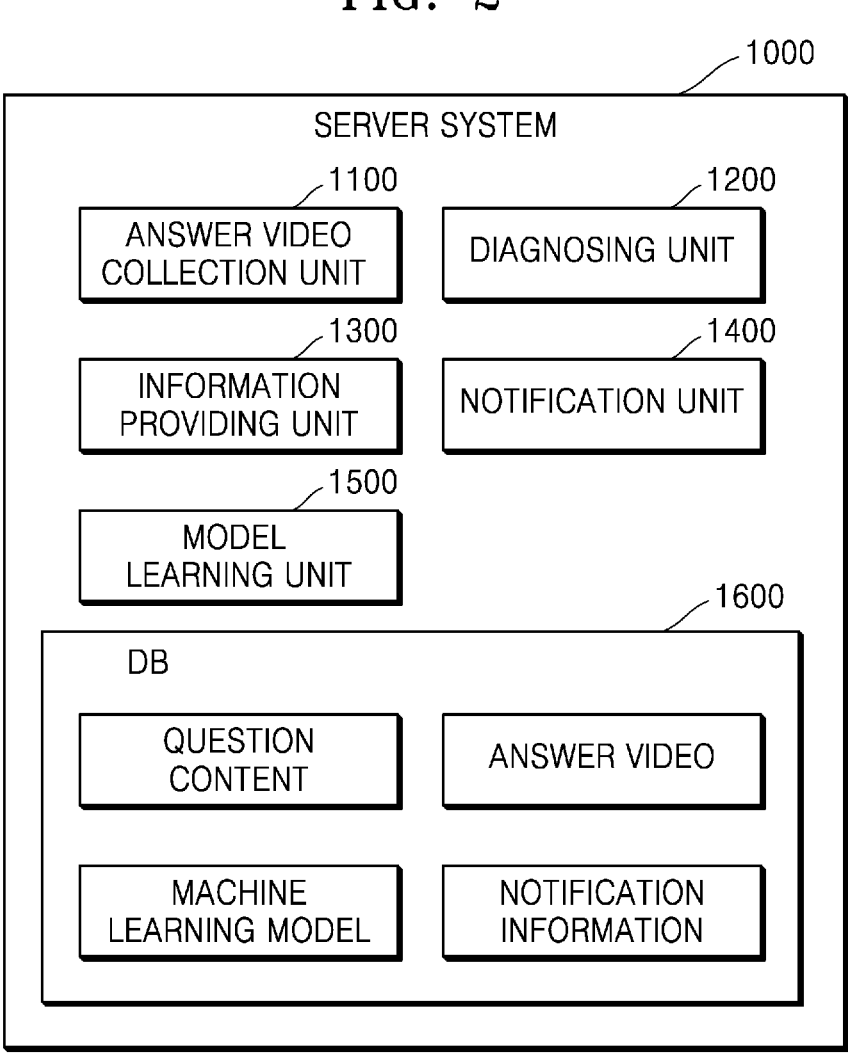
FIG. 2 schematically shows the internal configuration of a server system according to one embodiment of the present invention.

Hereinafter, embodiments of the present invention will be described in detail with reference to the accompanying drawings, so that a person having ordinary skill in the art may easily carry out the present invention. However, the invention may be embodied in various different forms and is not limited to the embodiments described herein. In addition, parts irrelevant to the description are omitted in the drawings to clearly describe the present invention, and like reference numerals designate like parts throughout the specification.

Throughout the specification, when a part is "connected" to another part, the above expression includes not only "directly connected" but also "electrically connected" in which another element is interposed therebetween. In addition, when a part "includes" a certain component, the above expression does not exclude other elements, but may further include the other elements, unless particularly stated otherwise.

In addition, the terms including an ordinal number such as first and second may be used to describe various elements, however, the components are not limited by the terms. The terms are used only for the purpose of distinguishing one component from another component. For example, the first component may be referred to as the second component without departing from the scope of the present invention, and similarly, the second component may also be referred to as the first component. The term "and/or" includes any one of multiple relevant listed items or a combination thereof.

In the present specification, the term 'unit' includes a unit implemented by hardware, a unit implemented by software, and a unit implemented by both of the hardware and the software. In addition, one unit may be implemented using at least two pieces of hardware, and at least two units may be implemented by one piece of hardware. In addition, "~unit" may not be limited to software or hardware, may be configured to be disposed in an addressable storage medium, and may be configured to reproduce at least one processor. Accordingly, as an example, the '~unit' includes components such as software components, object-oriented software components, class components, and task components, processes, functions, attributes, procedures, subroutines, segments of program code, drivers, firmware, microcode, circuits, data, databases, data structures, tables, arrays and variables. The functionality provided within the components and the '~unit's may be combined into a smaller number of components and '~unit's or further separated into additional components and the '~unit's. In addition, the components and '~unit's may be implemented to reproduce at least one CPU in a device or a secure multimedia card.

The 'patient terminal' and 'medical staff terminal' mentioned below may be implemented as a computer or portable terminal that can access a server or other terminals through a network. The computer includes, for example, a notebook computer, a desktop, a laptop, and the like installed with a web browser, the portable terminal refers to a wireless communication device that guarantees portability and mobility for example, and may include all kinds of hand-held-based wireless communication device such as personal communication system (PCS), global system for mobile communications (GSM), personal digital cellular (PDC), personal handyphone system (PHS), personal digital assistant (PDA), international mobile telecommunication (IMT)-2000, code division multiple access (CDMA)-2000, W-code division multiple access (W-CDMA), wireless broadband internet (Wibro) terminal. In addition, "network" may be implemented by all types of wired network such as a local area network (LAN), a wide area network (WAN) or a value added network (VAN), and wireless network such as a mobile radio communication network, or a satellite network.

Figure 1:
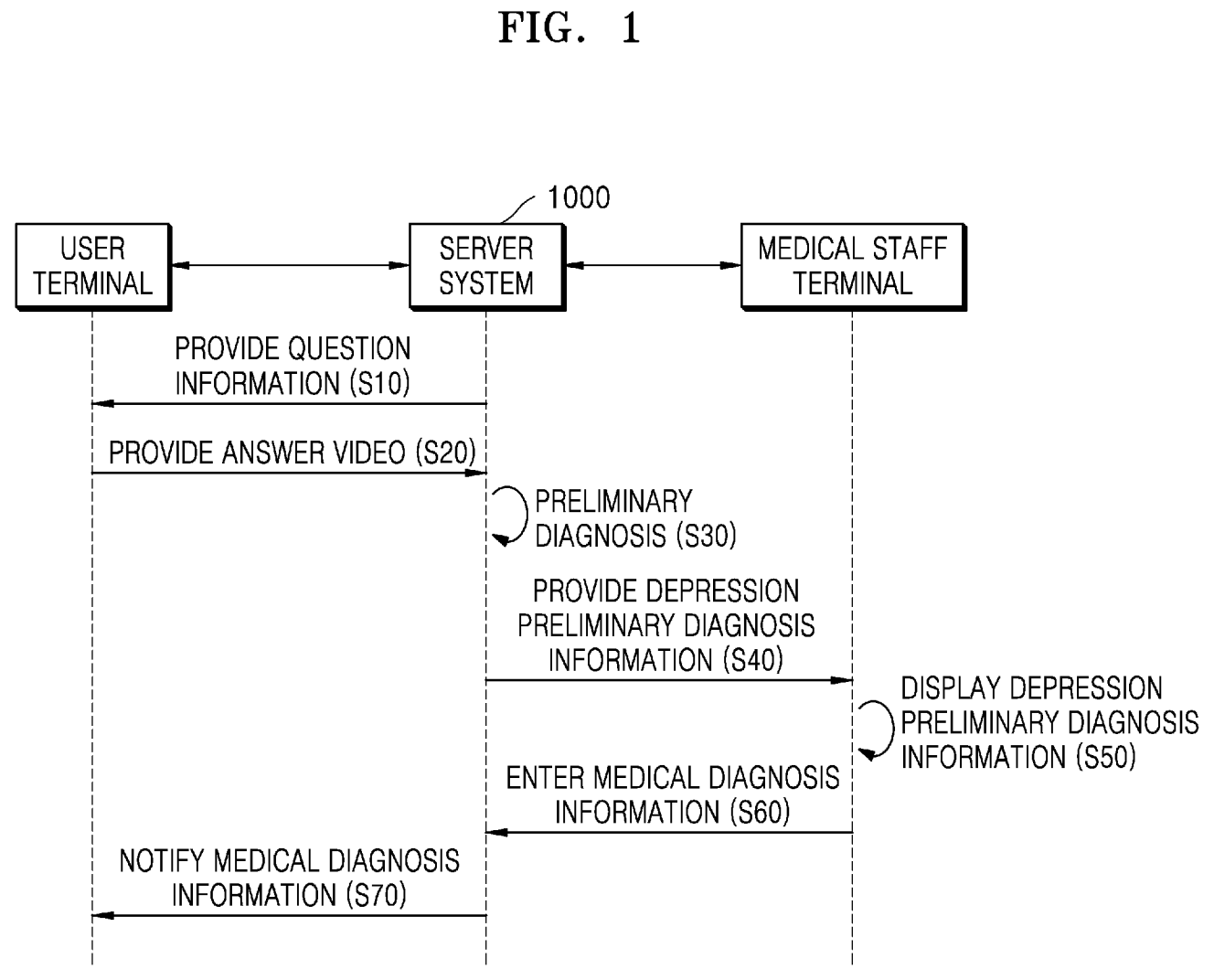

FIG. 1 schematically show overall steps performed in a system for providing depression preliminary diagnosis information according to one embodiment of the present invention.

The method for providing depression preliminary diagnosis information is provided using a machine learning model performed on a computing device having at least one processor and at least one memory.

In step S10, a server system 1000 provides question information to a patient terminal. The question information corresponds to information including at least one of text, voice, and video, and may be presented by text, video or voice only, or presented as media in the form obtained by synthesizing voice to a virtual human agent. In the specification herein, the "patient" may be understood in a broad sense as a person to be evaluated or a person to be diagnosed who provides an answer video. The subject diagnosed on depression may be referred to as "patient" for convenience of description in the present specification. However, the patient refers to an example of a person to be evaluated other than the patient as a concept in the hospital. For example, when the system according to the present invention is applied to organizations such as companies, all employees who want to be diagnosed will be understood as the category of "patient" according to the present specification.

In step S20, an answer video captured using a camera and a microphone in the patient terminal is transmitted to the server system 1000.

In the embodiments of the present invention, S10 and S20 are performed and then S10 and S20 are performed again for other questions, so that the server system 1000 may receive multiple answer videos.

In step S30, a diagnosing step, of deriving depression preliminary diagnosis information by using a machine-learned model for at least one answer video, is performed.

The diagnosis in the present specification refers to deriving of information related to mental illness such as depression based on the patient's answer video, and will be interpreted in the broadest sense that includes deriving a type, degree and the like of depression of the patient, or deriving a determination basis on the type, degree and the like of depression of the patient, from information for determining a presence of depression of the patient. In addition, the depression preliminary diagnosis information will be interpreted in the broadest sense that includes results on the above diagnosis as well as all of detailed information, comprehensive information, and processed information related to the diagnosis.

Step S40 includes performing: a providing step of providing the depression preliminary diagnosis information to a user.

The user may be any person including medical staff such as a mental health specialist and a nurse, a counselor or a person to be evaluated who filmed a corresponding interview video, an administrator or member of an organization related to work or the like of the person being evaluated.

In step S50, depression preliminary diagnosis information received from a medical staff terminal is displayed by a special user interface (UI). In step S50, it is assumed that the user is the medical staff. However, the scope of application of the present invention is not limited thereto, and various types of users may be provided with the depression preliminary diagnosis information. However, hereinafter, the user provided with the depression preliminary diagnosis information will be described as the medical staff for convenience of description. In addition, in the case of the subject to be evaluated, the patient terminal may be displayed on the same terminal as the medical staff terminal or the same application program.

In the terminal of the user such as medical staff, counselor or administrator the results primarily evaluated by the machine learning model and the basis for the results may be summarized and viewed through the depression preliminary diagnosis information, without viewing the entire answer video captured by the patient terminal. In step S50 described later, the screen displayed on the medical staff terminal corresponds to a form in which the medical staff may intuitively check a state of the patient. The medical staff may primarily receive preliminary information from the screen displayed in the above manner, and points on the screen determined as important by the medical staff may be efficiently checked, so that the medical staff can remotely conduct medical treatment for the patient, and time for the treatment can be efficiently used.

In step S60, the corresponding diagnosis information is input by the medical staff and transmitted to the server system 1000. The diagnosis information may include information on whether the patient needs to actually visit a hospital or information related to a hospital diagnosis appointment, in addition to diagnosis information on depression. Because the diagnosis information on depression is usable to train the machine learning model, the diagnosis information may be used as input data to a model learning unit 1500.

In step S70 the diagnosis information input by the medical staff in the server system 1000 is partially or entirely transmitted to the patient terminal. In the above process, the preliminary diagnosis information may be partially or entirely provided to the patient terminal in a processed form. Through the above process, the patient may receive information diagnosed by the machine learning model and/or information diagnosed by actual medical staff on depression of the patient, and/or information related to a reservation with a hospital.

In some embodiments of the invention, the server system 1000 may be composed of multiple computing systems. Alternatively, the patient terminal and/or the medical terminal may have a form physically coupled to the server system 1000 or correspond to a separate terminal.

FIG. 2 schematically shows the internal configuration of the server system 1000 according to one embodiment of the present invention.

The answer video collection unit 1100 corresponds to a module that performs the above-mentioned S10 and S20. Preferably, the answer video collection unit 1100 may perform S10 in the form of structured questions, or it may proceed in the form of selecting a question by using analysis results on the answer video of the user.

The answer videos collected by the answer video collection unit 1100 are stored in a DB 1600 of the server system 1000.

The diagnosing unit 1200 derives depression preliminary diagnosis information for at least one answer video by using the machine learning model.

Specifically, the machine learning model may include various detailed machine learning models that perform an evaluation on the answer video performed by the person to be evaluated (the patient). The detailed machine learning model may correspond to a detailed machine learning model trained based on deep learning to perform an evaluation, or may correspond to a detailed machine learning model for deriving feature information on the corresponding answer video according to a predetermined routine or algorithm other than learning and performing an evaluation on the derived feature information.

In one embodiment of the present invention, the diagnosing unit 1200 basically receives an answer video performed by the subject (patient) and including multiple continuous video (image) information and voice information and derives depression preliminary diagnosis information by using a machine learning model trained through the machine learning technology such as deep learning. In addition, in some processes, the diagnosing unit 1200 may additionally analyze the answer video based on preset rules other than the machine learning and derive specific evaluation values. The diagnosing unit 1200 may extract video and voice information from an answer video containing multiple continuous videos (images) and voice, and input the extracted video and voice information into each detailed machine learning model, thereby deriving a result value, or integrate the video and voice information and input the integrated the video and voice information into a detailed machine learning model, thereby deriving a result value.

The information providing unit 1300 provides the depression preliminary diagnosis information to the user. Details thereof will be described later.

A notification unit 1400 corresponds to a module that performs the above-described steps S60 and S70.

The model learning unit 1500 corresponds to a module for continuously training the machine learning model used for diagnosis using learning data in the diagnosing unit 1200 described above. Medical staff diagnosis information (S60) may be utilized as learning data.

In addition, the DB 1600 stores question content for question information presented to the patient terminal by the answer video collection unit 1100, an answer video received from the answer video collection unit 1100, a learned machine learning model for performing diagnosis in the diagnosing unit 1200, and notification information related to the execution of steps S60 and S70.

In another embodiment of the present invention, the server system 1000 may include at least two servers, each server may include some of the above-described components, and each server may communicate to perform the method for providing depression preliminary diagnosis information by using the machine learning model For example, functions related to the answer video collection unit 1100 may be included in a specific server and functions related to the diagnosing unit 1200 and the model learning unit 1500 may be included in the other specific server, so that the method for providing depression preliminary diagnosis information by using the machine learning model according to the present invention may be performed through communication between the specific server and the other specific server.

Figure 3:
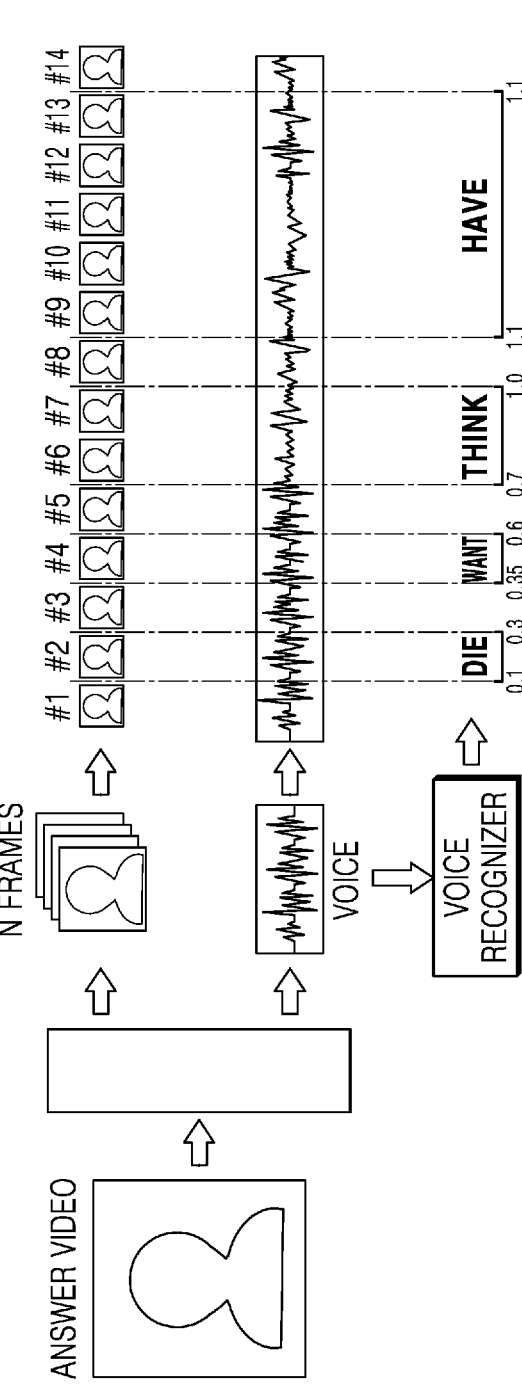
FIG. 3 schematically shows a process of a first step performed by a diagnosing unit according to one embodiment of the present invention.

FIG. 3 schematically shows a process of a first step performed by a diagnosing unit 1200 according to one embodiment of the present invention.

In an exemplary embodiment of the present invention, the diagnosing step derives the depression preliminary diagnosis information is derived from the answer video by using the machine-learned model, based on multiple words extracted from text of a voice, multiple image frames corresponding to the words, respectively, and multiple pieces of voice information corresponding to the words, respectively.

In the first step shown in FIG. 3, multiple words extracted from text of a voice, multiple image frames corresponding to the words, respectively, and multiple pieces of voice information corresponding to the words, respectively, are extracted from the answer video.

Specifically, in the first step, video information and voice raw data are separated from the answer video. Specifically, the diagnosing unit 1200 includes a video/voice separation module, and the video/voice separation module separates the corresponding answer video into video information and voice raw data.

The diagnosing unit 1200 includes an STT module and the STT module may perform speech-to-text (STT) conversion on the input answer video, so as to derive text information about the voice of the answer video performed by the user. The speech-to-text conversion performed by the STT module may be performed by using various existing STT conversion schemes.

In the exemplary embodiment of the present invention, a voice recognized by a voice recognizer is separated by morpheme (or word), a video image matching with each morpheme and raw voice data according to a specific section are extracted.

For example, in the embodiment shown in FIG. 3, a total of four morphemes "die", "want", "think" and "have" are derived, and image frames corresponding to the morphemes are selected, respectively. In FIG. 3, the image frame at a point at which a pronunciation of the corresponding morpheme starts is selected. However, the present invention is not limited thereto, and at least one image frame related to the corresponding morpheme may be selected. The above scheme is equally applied to voice information according to a specific section.

In other words, according to the present invention, the sequence for each morpheme recognized by the speech recognizer is handled other than equally handling all time sequences, so that the computational load can be reduced while increasing the accuracy in a multimodal analysis in which the voice information is present.

In the embodiment shown in FIG. 3, the image frames and the raw speech data are extracted while matching the sequence with each morpheme recognized by the speech recognizer. However, in another embodiment of the present invention, the rest of the information may be extracted while matching the sequence with the image frame, time or the like, and an alignment may be used, so that initial data can be obtained.

On the other hand, in another embodiment of the present invention, unlike the embodiment shown in FIG. 3, each of image frames, voice raw data, and text (morphemes) may be input to a multi-modal model (models of FIGS. 4 and 5) without performing the alignment between the image frames, voice raw data, and text (morphemes), so as to derive results. In this case, each data may be used entirely or sampled according to preset rules.

In another embodiment of the present invention, input data may be extracted by using at least one, preferably at least two, of image frames, voice raw data, and text. For example, the determination may be performed only with image frames and raw voice data without considering information about text.

Figure 4:
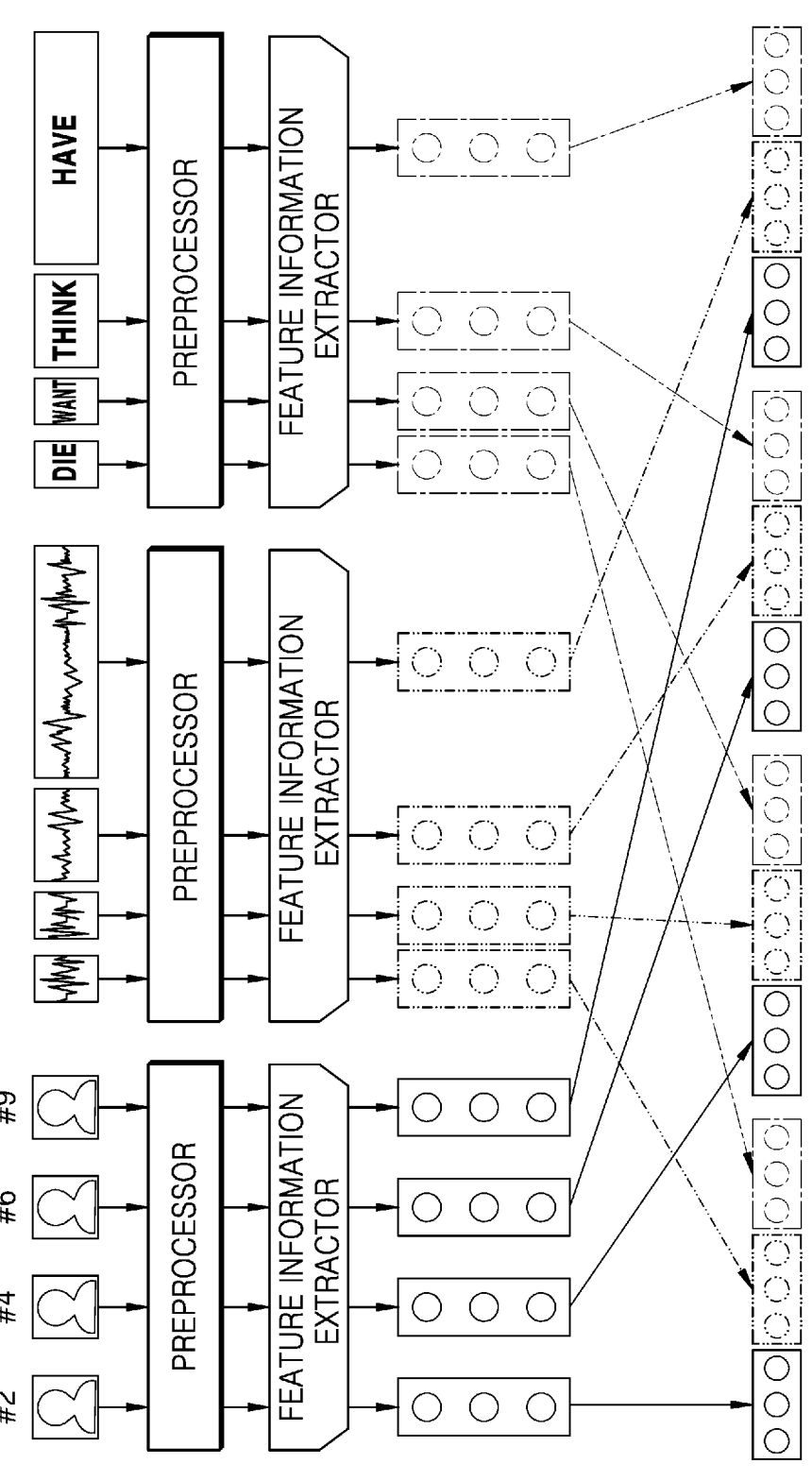
FIG. 4 schematically shows a process of a second step performed by the diagnosing unit according to one embodiment of the present invention.

FIG. 4 schematically shows a process of a second step performed by a diagnosing unit 1200 according to one embodiment of the present invention.

step 2, includes performing a step of deriving a second step of deriving multiple pieces of first feature information, multiple pieces of second feature information, and multiple pieces of third feature information, from the words, the image frames, and the pieces of voice information by using each detailed machine learning model.

The voice information includes at least one of raw data for voice and at least one piece of voice feature information extracted from the raw data for voice.

Specifically, in step 2, the words, the image frames and the pieces of voice information are preprocessed through each preprocessor. Thereafter, first feature information, second feature information, and third feature information for each input data are derived through an extractor for extracting data rows by performing an FC process on information in which the preprocessed data is derived through a feature information extractor, for example, a CNN module. The feature information extractor extracts feature information according to at least one of a machine learning model and an algorithm according to preset rules. In addition, according to the embodiments, the preprocessor may be partially omitted in each of the word, image frame, and voice information.

Detailed feature information may be extracted from voice text information by performing embedding for expressing text information as a vector. In addition, an embedded vector for a corresponding question may be additionally input to the feature information extractor for voice information or the RNN module shown in FIG. 5. Accordingly, The detailed machine learning model may derive more sophisticated third feature information by considering not only the answer image but also the question about the answer video.

In some embodiments of the invention, an embedding module included in the feature information extractor for voice information may express each text information into a vector form by using various embedding schemes such as One-hot encoding, CountVectorizer, TfidVectorizer and Word2Vec.

Thus, in the exemplary embodiment of the present invention, the video information, voice feature information, and text information of the answer video may be respectively input to the machine learning model, so as to figure out the context and intention of the user's answer in the answer video which is difficult to figure out only by the text, so that more accurate depression diagnosis information can be derived.

Preferably, the video information (image frame) and the voice raw data separated by the video/voice separation module are individually preprocessed and input to the machine learning model. The preprocessing module included in the diagnosing unit 1200 preprocesses each of the voice information and the voice raw data. Accordingly, the video information and the voice information are converted into a form suitable for the algorithm of the machine learning model through the preprocessing module, and thus the performance of the machine learning model can be improved.

To this end, in the preprocessing module, missing values or features are processed through a data cleaning step for the video information and the voice information, and encoded into numeric data by one hot encoding scheme through a handling text and categorical attributes step, the data is converted through a custom transformers step, and a range of the data is set through a feature scaling step, and the above steps may be automated through a transformation pipelines step. The steps performed by the preprocessing module are not limited to the above steps, and may include various preprocessing steps for machine learning models.

Figure 5:
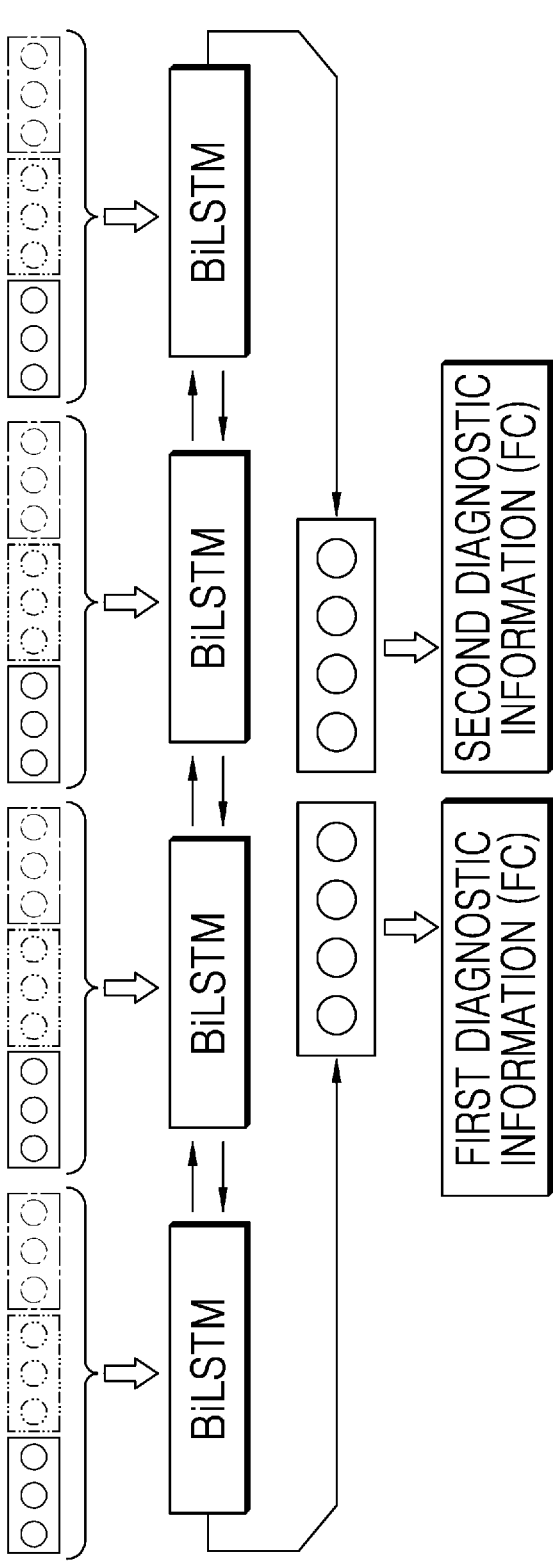
FIG. 5 schematically shows a process of a third step performed by the diagnosing unit according to one embodiment of the present invention.

FIG. 5 schematically shows a process of a third step performed by a diagnosing unit 1200 according to one embodiment of the present invention.

Step 3 includes performing a step of deriving derived information including a degree of depression from the pieces of first feature information, the pieces of second feature information, and the pieces of third feature information by using an artificial neural network.

The artificial neural network includes multiple machine-learned inference modules. When the four morphemes are present as shown in FIG. 3, first feature information of the image frame for the first morpheme, second feature information for the voice feature information for the first morpheme, and third feature information for the first morpheme text are input to a first inference module in a concatenated (CONCAT) form, and the first feature information, the second feature information, and the third feature information for the remaining second, third, and fourth morphemes are also processed in the same manner.

In the embodiment shown in FIG. 5, each feature information input to the artificial neural network corresponds to an aligned state. However, in another embodiment of the present invention, the feature information may be input to the artificial neural network in a form that is not aligned.

Preferably, the artificial neural network corresponds to an artificial neural network considering sequence data, and more preferably, corresponds to a recurrent neural network or transformer-based model. In this case, the first feature information, the second feature information, and the third feature information corresponding to each of the words are input to the detailed module of the artificial neural network in a merged form. More preferably, the transformer-based model includes a transformer series machine learning model based on the attention mechanism.

The above recurrent neural networks or transformer-based machine learning models may finally output an inference result of multiple data rows, and the data rows may include first diagnosis information, second diagnosis information, . . . , and Nth diagnosis information. The above diagnosis information may include depression prediction information and/or depression type.

The inference result may include multiple inference results. For example, final diagnosis information as shown in FIG. 5 may be derived from multiple words extracted from text of a voice for each specific section with respect to entire at least one answer video, multiple image frames corresponding to the words, respectively, and multiple pieces of voice feature information corresponding to the plurality of words, respectively.

A depression prediction score and/or a depression type may be checked for each specific section based on the above each final diagnosis information. When the checked score and/or type are gathered as a whole, it may be checked where the high depression prediction score is output in the entire interview video, or which type of depression is exhibited when the high depression prediction score is output.

Preferably, in one embodiment of the present invention, the diagnosing unit 1200 may derive overall evaluation information by gathering the depression prediction score and/or the depression type in each final diagnosis information.

Alternatively in another embodiment of the present invention, information on a part in which the cause of depression is predicted (for example, a video position or a text position) in the final diagnosis information of FIG. 5 may be included and output.

In this manner, according to the present invention, determination results as well as detailed information on the basis of the determination results for all answer videos or individual answer videos may be simply provided to the medical staff, and the medical staff may immediately check only the corresponding part or play the related video part, so that the diagnosis can be more efficiently conducted.

In another embodiment of the present invention, the depression preliminary diagnosis information may be derived by using the machine-learned model, based on at least two pieces of information among multiple words, multiple image frames, and voice information extracted from text of a voice extracted from the answer video.

In another embodiment of the present invention, the depression preliminary diagnosis information may be derived by using the machine-learned model, based on the image frames and the pieces of voice information extracted from the answer video. In this case, the diagnosing unit includes a diagnosis, prediction or inference model based on the image frames and the voice information, check an accurate part of the position affecting the inference result (that is, affecting the score) by using interpretability techniques (such as Grad-CAM and Integrated Gradient) and then obtain the time thereof, estimate a position of the corresponding text, and show the position in FIGS. 6, 7, 8 and the like.

Figure 6:
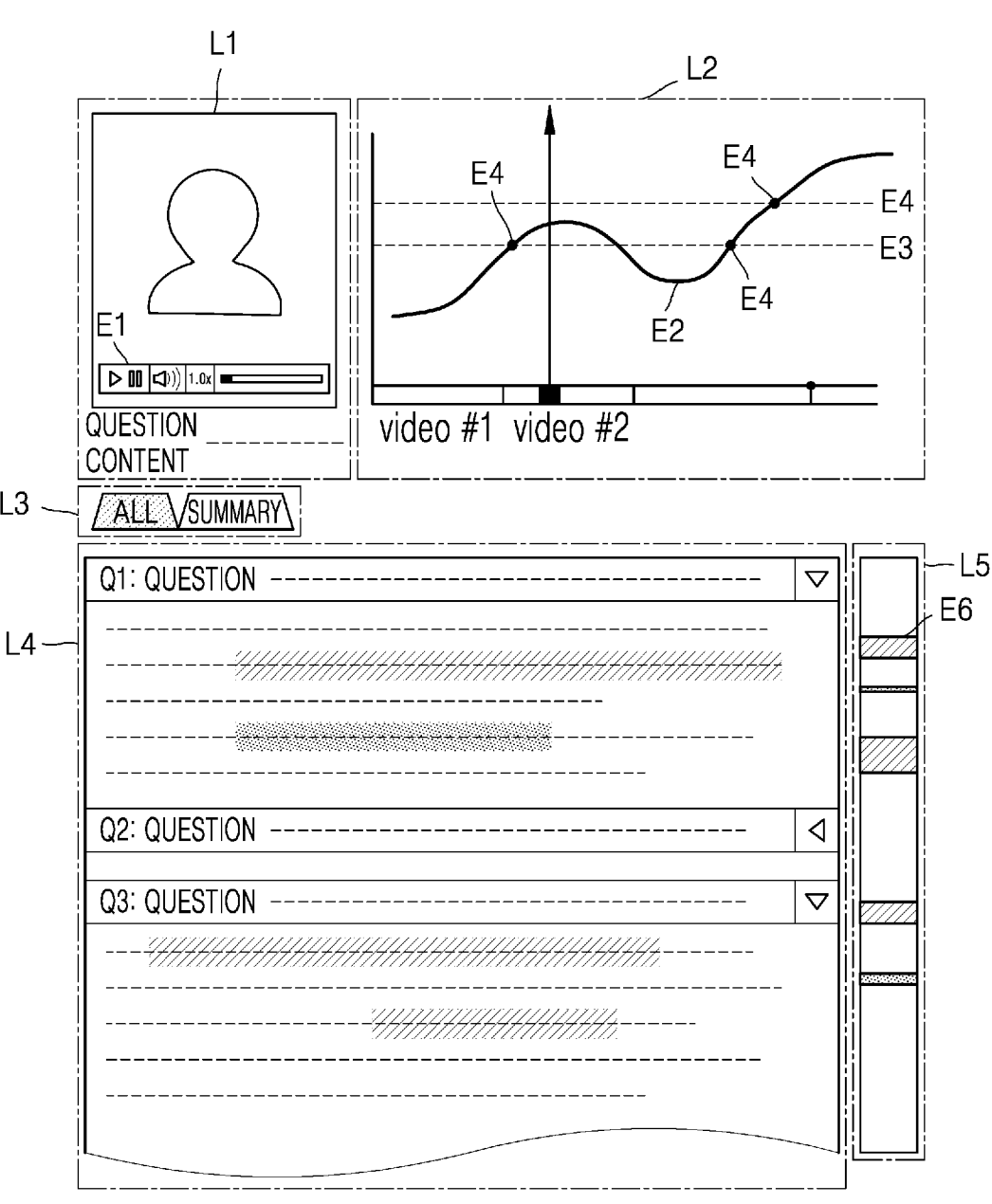
FIG. 6 schematically shows a first display screen according to one embodiment of the present invention.

FIG. 6 schematically shows a first display screen according to one embodiment of the present invention.

The method for providing depression preliminary diagnosis information includes: a providing step of providing the depression preliminary diagnosis information to a user.

A first display screen displayed by the providing step includes: an answer video layer L1 for displaying the answer video; and a script layer L4 for displaying question information related to the answer video and answer text information extracted from the answer video, wherein a video time point of the answer video layer L1 may be changed to a time point corresponding to a position of a script part selected according to an input by the user in the script layer L4.

The first display screen may be displayed on a terminal of the medical staff or a terminal of the person to be evaluated (the patient) as needed.

The answer video layer L1 corresponds to a layer for playing the answer video, and the user (such as medical staff, counselor and administrator) may select play/pause, control a play speed, and change a play point in the video. The above functions may be performed by inputting a control element E1.

In the script layer L4, the patient's voice text converted to text through the STT in the diagnosing unit 1200 is displayed. In the above manner, the medical staff may quickly check the answers of the patient, the person to be diagnosed, or the person to be evaluated. When a part of the answer determined as important by the medical staff is clicked or selectively input, the video time point of the answer video layer L1 may be shifted to a corresponding video time point, so that the actual video can be quickly checked.

Preferably, the first display screen includes: a depression graph layer L2 for displaying a degree of depression diagnosed according to a time axis, wherein a video time point of the answer video layer L1 may be changed to a time point corresponding to a position on the time axis selected according to an input by the user in the depression graph layer L2.

In the above interface, when the user selects a part with a high degree of depression determined in the depression graph layer L2, the play time point of the video of the answer video layer L1 may be automatically changed, so that only the parts determined by the machine learning model as having depressive factors may selectively identified. Accordingly, the important parts related to depression can be quickly checked without viewing all the answer videos, and the medical staff can make judgment about the reason for the determination derived by the machine learning model and decide whether to accept the determination.

Preferably, the part of the answer text displayed on the script layer L4 is displayed with change in at least one of highlight, font, size, color, and underline according to at least one of a degree of depression and a type of depression in the depression preliminary diagnosis information corresponding to the corresponding part of the answer text.

In the above manner, the medical staff may identify the reason for the determination by the diagnosing unit 1200, intuitively identify the degree of depression determined by the diagnosing unit 1200 and exceeding a predetermined reference or the text part related to depression, and quickly play the video for the part determined as important without playing the entire answer video.

Preferably, the depression graph layer L2 includes: a first reference display element E3 indicating that the degree of depression exceeds a predetermined first reference; and a second reference display element E4 indicating that the degree of depression exceeds a predetermined second reference.

The first reference display element E3 may correspond to a mild degree of depression border, and the second reference display element E4 may correspond to a severe degree of depression. The above display interface can the user to efficiently navigate parts exceeding the reference value for the degree of depression. In other words, the first reference display element and the second reference display element may display detailed types of depression.

The first display screen further includes a scroll layer L5 for displaying scroll information of the script layer L4, the scroll layer L5 displays an information display element E6 at each time point displayed according to at least one of the degree of depression and the type of depression in the depression preliminary diagnosis information, and the answer video is shifted to a position of answer text corresponding to the selected information display element E6 in the script layer E4 when the user selects the information display element E6.

Preferably, the color, size, shape and the like of the information display element E6 may be changed according to at least one of the degree of depression and the type of depression. Accordingly, the medical staff can intuitively graphically determine the overall degree of depression of the patient, and quickly shift a position to the position determined as a high degree of depression.

In addition, when the content of the text is long in the answer video, all text may not displayed on one screen. In this case, the user may use the scroll layer L5, so that the video can be shifted to the text and the video play time point wanted by the user.

Figure 10:
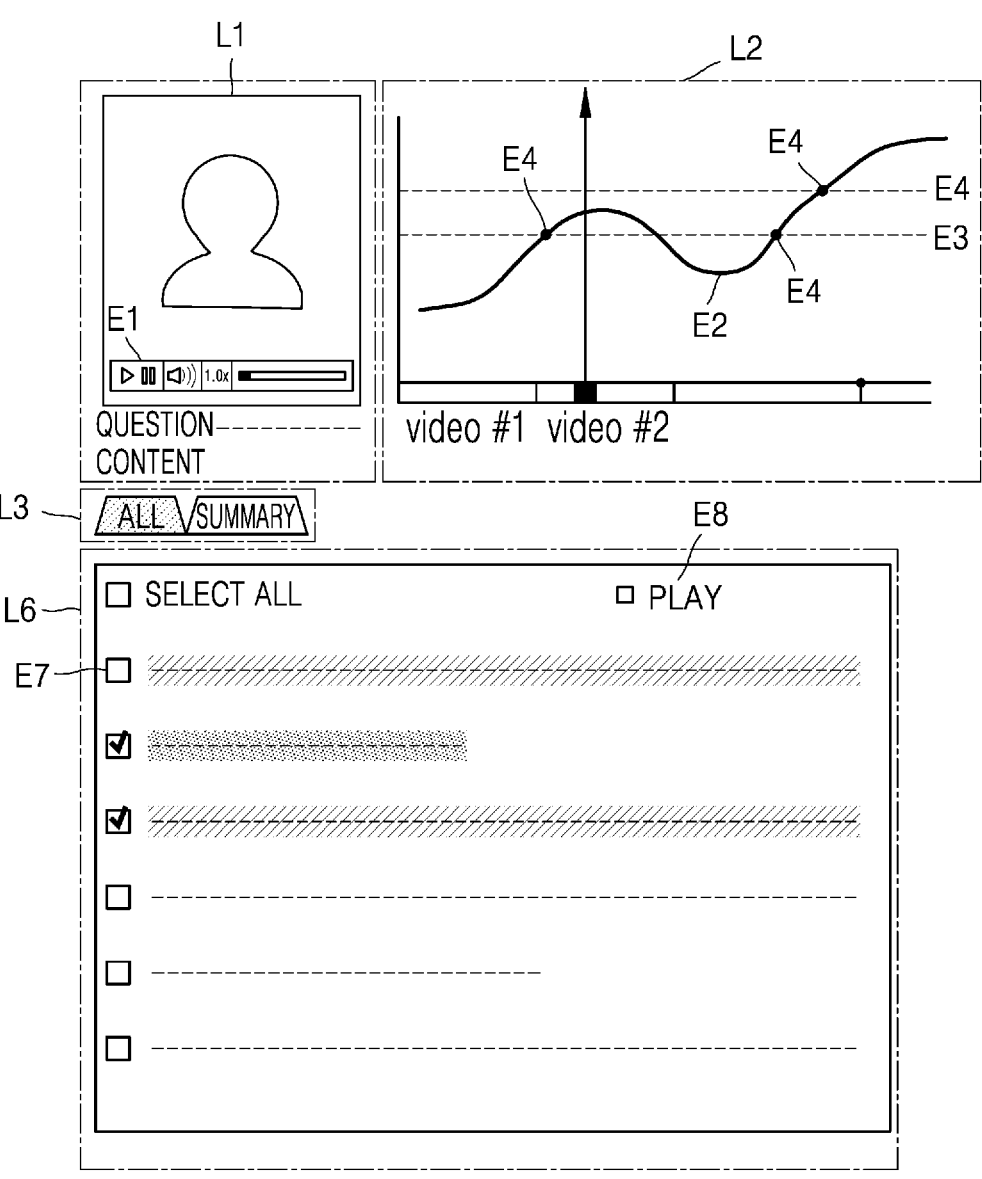
FIG. 10 schematically shows a second display screen according to one embodiment of the present invention.

The page selection layer L3 provides an interface for entering a shift to a page for the All shown as in FIG. 6 and a page for the Summary shown as in FIG. 10.

According to the configuration of the first display screen as described above, the medical staff may check important parts without individually checking multiple answer videos, quickly check whether the basis determined by the machine learning model is reasonable, and identify overall evaluation results for long-term videos, so that more accurate determination on depression can be efficiently performed.

Figure 7:
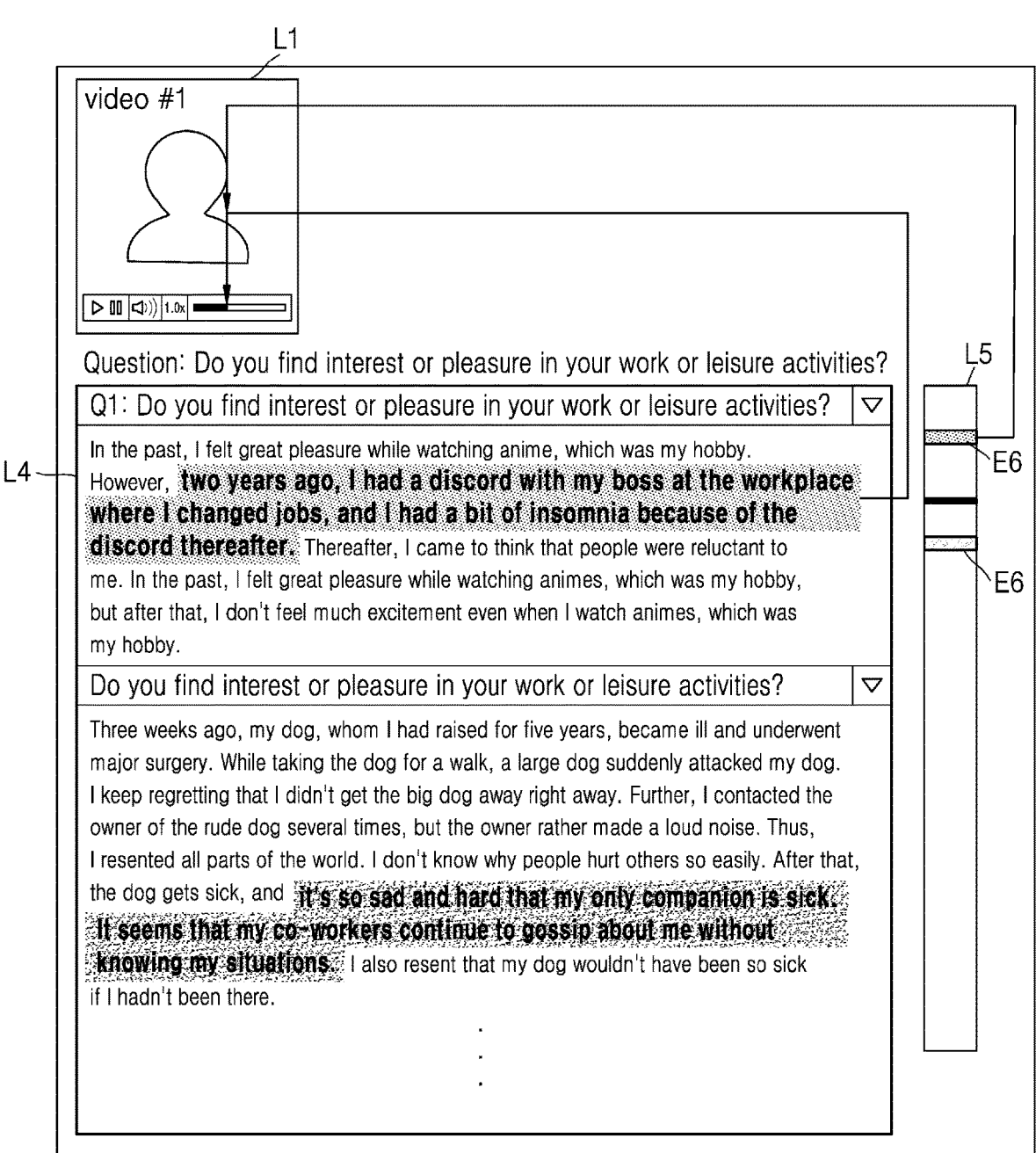
FIG. 7 schematically shows an answer video layer and a script layer according to one embodiment of the present invention.
Figure 8:
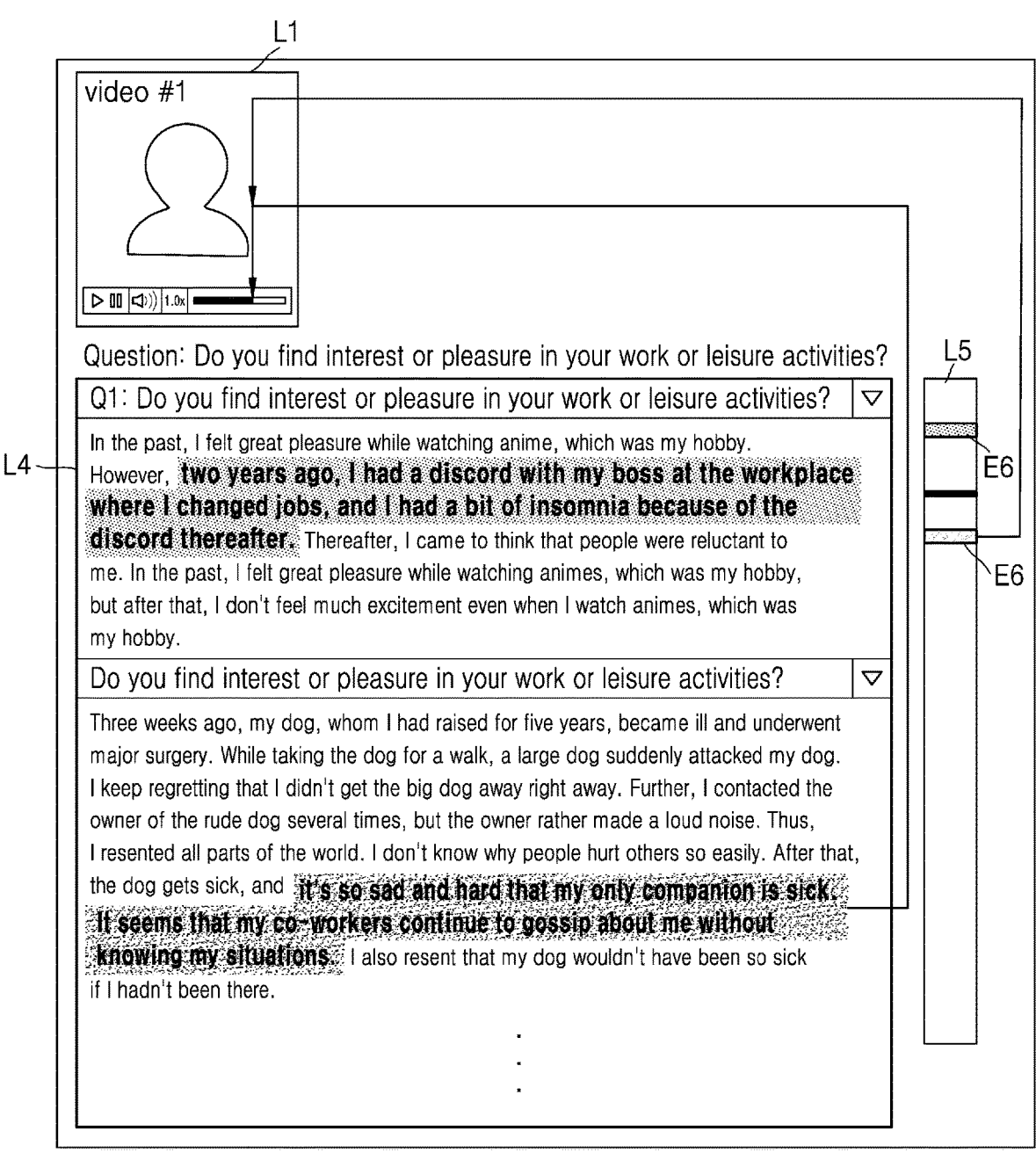
FIG. 8 schematically shows an answer video layer and a script layer according to one embodiment of the present invention.

FIG. 7 schematically shows the answer video layer L1 and the script layer L4 according to one embodiment of the present invention. FIG. 8 schematically shows the answer video layer L1 and the script layer L4 according to one embodiment of the present invention.

As shown in FIG. 7, the answer image layer L1 displays a video at one specific time point of multiple answer videos. In addition, the script layer L4 displays text information on the answer of the patient for each question.

As described above, the form of displaying the text according to the at least one of the type and degree of depression diagnosed by the diagnosing unit 1200 is changed as shown in FIG. 7, and this is also reflected in the scroll layer L5 to display the information display element E6.

The part of the answer text displayed with the change in at least one of the highlight, font, size, color, and underline corresponds to a state in which the degree of depression of the depression preliminary diagnosis information corresponding to the part of the answer text is a predetermined reference or more, and the video time point of the answer video layer L1 is changed to a time point corresponding to a position of the part of the answer text when the user selects the part of the answer text displayed with the change in at least one of the highlight, font, size, color, and underline.

The highlighted color on the upper side and the highlighted color on the lower side in FIG. 7 corresponds colors selected according to the type of depression. The type of depression may include, for example, melancholia type, atypical depression, adolescent depression, elderly depression, alcoholism-accompanying depression, and menopausal depression.

The screen shown in FIG. 7 illustrates a state in which the video play time point of the answer video layer L1 is changed when the upper side of the script layer L4 is selected and input, and the screen shown in FIG. 8 illustrates a state in which the video play time point is also changed as video No. 1 of the answer video layer L1 is changed to No. 2 when the lower side of the script layer L4 is selected and input.

Figure 9A:
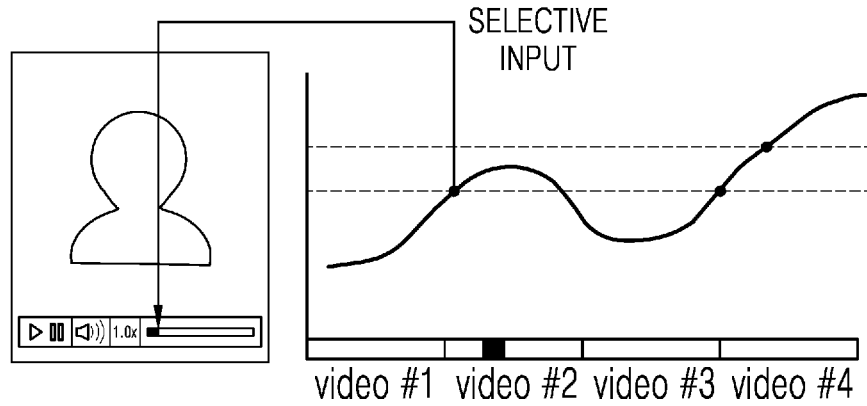
FIGS. 9A and 9B schematically show an answer video layer and a depression graph layer according to one embodiment of the present invention.
Figure 9B:
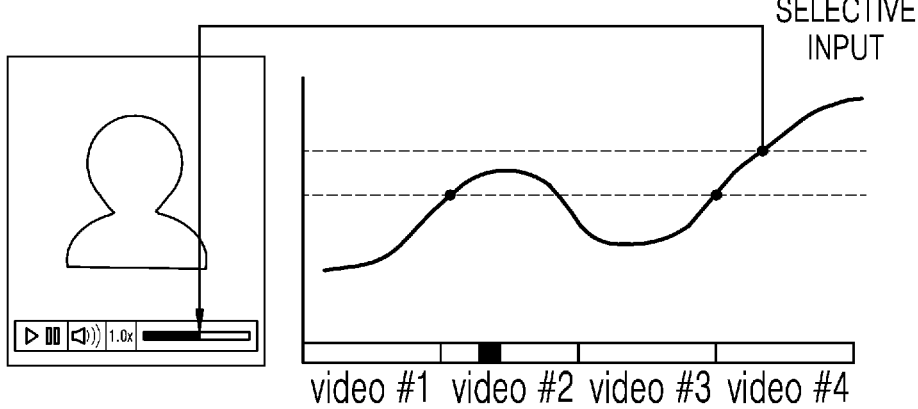

FIGS. 9A and 9B schematically show the answer video layer L1 and the depression graph layer L2 according to one embodiment of the present invention.

As described above, the first display screen includes a depression graph layer L2 for displaying a degree of depression diagnosed according to a time axis, wherein and a video and/or a video time point of the answer video layer L1 may be changed to a video and/or a time point corresponding to a position on the time axis selected according to an input by the user in the depression graph layer L2.

FIG. 10 schematically shows the second display screen according to one embodiment of the present invention.

Preferably, the second display screen shown in FIG. 10 corresponds to a screen displayed when the user selects the summary part in the page selection layer L3.

A second display screen displayed by the providing step includes: an answer video layer L1 for displaying the answer video; and a summary script layer L6 for displaying summary answer text information extracted from the answer video.

Preferably, the summary answer text information includes at least one part of the answer text in which the degree of depression in the depression preliminary diagnosis information corresponding to the part of the answer text is the predetermined reference or more.

Preferably, the video time point of the answer video layer L1 may be changed to a time point corresponding to a position of a script part selected according to an input by the user in the summary script layer L6.

The above-described scroll layer L5 may also be displayed on the second display screen.

The second display screen further include at least one selection input element corresponding to each of the summary answer text information, wherein a part of multiple answer videos corresponding to a part of the selection input element or the summary answer text information selected according to an input of the user may be played.

Preferably, the second display screen further includes at least one checkbox E7 corresponding to each of the summary answer text information. For example, in FIG. 10, each check box E7 is displayed at a position corresponding to each summary answer text information. The check box E7 may correspond to an example of the selection input element.

Preferably, Parts of multiple (or one or more) answer videos corresponding to multiple pieces of summary answer text information in which the user selects the checkbox E7 may be played according to an input of the user. Alternatively in another embodiment of the present invention, multiple (or one or more) parts, that is, sentences and the like of the summary answer text information may be selected and parts of the answer video corresponding to the selected parts may be played.

Specifically, in one embodiment of the present invention, when the user selects the checkbox E7 for the script to be played, which is wanted by the user in the summary script layer L6, and then selects an element E8 indicated for Play, the script selected with the checkbox E7 is played. The above play may be performed as repeated play.

In other words, the second display screen collects and displays scripts determined by the diagnosing unit 1200 as having a high degree of depression. In this state, only the parts selected by the user, that is, the parts of the video secondarily selected by the user for the inference result of the machine learning model are played, so that more accurate determination can be finally performed by using the determination results of the machine learning model while more easily conducting the diagnosis, even when the medical staff does not check the entire answer videos. Counselors may more clearly identify which part has a problem, so as to perform more accurate counseling to counselees.

Figure 11:
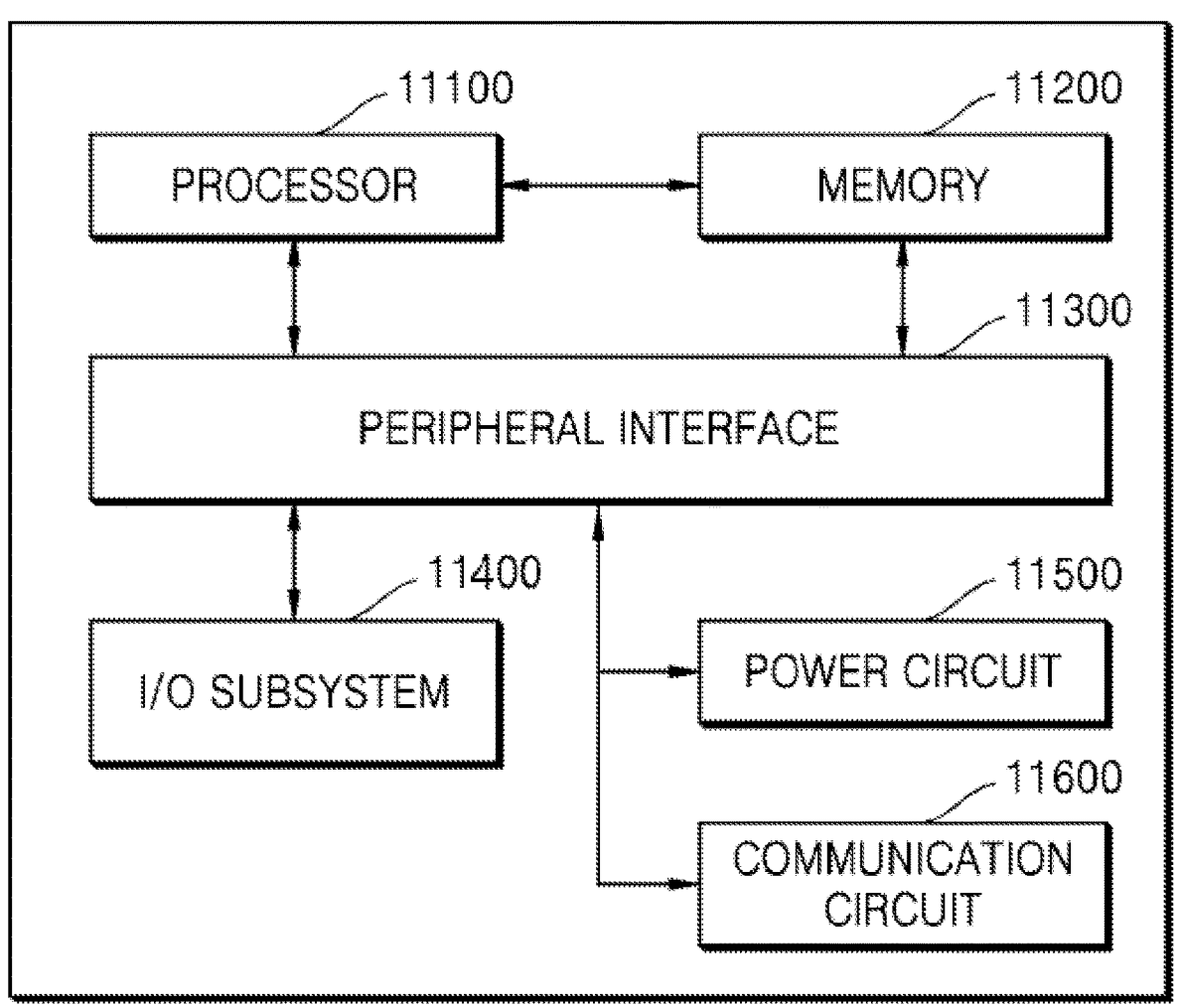
FIG. 11 shows a computing device which may correspond to a server system, a user terminal and the like according to one embodiment of the present invention.

FIG. 11 shows a computing device which may correspond to a server system, a user terminal and the like according to one embodiment of the present invention.

The server system 1000 shown in the above-described FIG. 2 may include components of the computing device 11000 shown in FIG. 11.

As shown in FIG. 11, the computing device 11000 may at least include at least one processor 11100, a memory 11200, a peripheral device interface 11300, an input/output subsystem (I/O subsystem) 11400, a power circuit 11500, and a communication circuit 11600. The computing device 11000 may correspond to the computing device 1000 shown in FIG. 1.

The memory 11200 may include, for example, a high-speed random access memory, a magnetic disk, an SRAM, a DRAM, a ROM, a flash memory, or a non-volatile memory. The memory 11200 may include a software module, an instruction set, or other various data necessary for the operation of the computing device 11000.

The access to the memory 11200 from other components of the processor 11100 or the peripheral interface 11300, may be controlled by the processor 11100.

The peripheral interface 11300 may combine an input and/or output peripheral device of the computing device 11000 to the processor 11100 and the memory 11200. The processor 11100 may execute the software module or the instruction set stored in memory 11200, thereby performing various functions for the computing device 11000 and processing data.

The input/output subsystem may combine various input/output peripheral devices to the peripheral interface 11300. For example, the input/output subsystem may include a controller for combining the peripheral device such as monitor, keyboard, mouse, printer, or a touch screen or sensor, if needed, to the peripheral interface 11300. According to another aspect, the input/output peripheral devices may be combined to the peripheral interface 11300 without passing through the I/O subsystem.

The power circuit 11500 may provide power to all or a portion of the components of the terminal. For example, the power circuit 11500 may include a power failure detection circuit, a power converter or inverter, a power status indicator, a power failure detection circuit, a power converter or inverter, a power status indicator, or any other components for generating, managing, and distributing the power.

The communication circuit 11600 may use at least one external port, thereby enabling communication with other computing devices.

Alternatively, as described above, if necessary, the communication circuit 11600 may transmit and receive an RF signal, also known as an electromagnetic signal, including RF circuitry, thereby enabling communication with other computing devices.

The above embodiment of FIG. 11 is merely an example of the computing device 11000, and the computing device 11000 may have a configuration or arrangement in which some components shown in FIG. 11 are omitted, additional components not shown in FIG. 11 are further provided, or at least two components are combined. For example, a computing device for a communication terminal in a mobile environment may further include a touch screen, a sensor or the like in addition to the components shown in FIG. 11, and the communication circuit 11600 may include a circuit for RF communication of various communication schemes (such as WiFi, 3G, LTE, Bluetooth, NFC, and Zigbee). The components that may be included in the computing device 11000 may be implemented by hardware, software, or a combination of both hardware and software which include at least one integrated circuit specialized in a signal processing or an application.

In the above, the method and system for providing preliminary diagnosis information based on depression of the present invention have been described, but The present invention can be used for various mental disorders, in this case, the term 'depression' can be replaced with 'mental illness'.

The methods according to the embodiments of the present invention may be implemented in the form of program instructions to be executed through various computing devices, thereby being recorded in a computer-readable medium. In particular, a program according to an embodiment of the present invention may be configured as a PC-based program or an application dedicated to a mobile terminal. The application to which the present invention is applied may be installed in the computing device 11000 through a file provided by a file distribution system. For example, a file distribution system may include a file transmission unit (not shown) that transmits the file according to the request of the computing device 11000.

The above-mentioned device may be implemented by hardware components, software components, and/or a combination of hardware components and software components. For example, the devices and components described in the embodiments may be implemented by using at least one general purpose computer or special purpose computer, such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and at least one software application executed on the operating system. In addition, the processing device may access, store, manipulate, process, and create data in response to the execution of the software. For the further understanding, some cases may have described that one processing device is used, however, it is well known by those skilled in the art that the processing device may include a plurality of processing elements and/or a plurality of types of processing elements. For example, the processing device may include a plurality of processors or one processor and one controller. In addition, other processing configurations, such as a parallel processor, are also possible.

The software may include a computer program, a code, and an instruction, or a combination of at least one thereof, and may configure the processing device to operate as desired, or may instruct the processing device independently or collectively. In order to be interpreted by the processor or to provide instructions or data to the processor, the software and/or data may be permanently or temporarily embodied in any type of machine, component, physical device, virtual equipment, computer storage medium or device, or in a signal wave to be transmitted. The software may be distributed over computing devices connected to networks, so as to be stored or executed in a distributed manner. The software and data may be stored in at least one computer-readable recording medium.

The method according to the embodiment may be implemented in the form of program instructions to be executed through various computing mechanisms, thereby being recorded in a computer-readable medium. The computer-readable medium may include program instructions, data files, data structures, and the like, independently or in combination thereof. The program instructions recorded on the medium may be specially designed and configured for the embodiment, or may be known to those skilled in the art of computer software so as to be used. An example of the computer-readable medium includes a magnetic medium such as a hard disk, a floppy disk and a magnetic tape, an optical medium such as a CD-ROM and a DVD, a magneto-optical medium such as a floptical disk, and a hardware device specially configured to store and execute a program instruction such as ROM, RAM, and flash memory. An example of the program instruction includes a high-level language code to be executed by a computer using an interpreter or the like as well as a machine code generated by a compiler. The above hardware device may be configured to operate as at least one software module to perform the operations of the embodiments, and vise versa.

According to one embodiment of the present invention, a method, a system, and a computer-readable medium for providing depression preliminary diagnosis information by using a machine learning model can be provided in which a result of analysis on depression with respect to an answer video performed by a person to be evaluated and supporting information therefor can be provided to medical staff through a special user interface, so as to enable the medical staff to more efficiently determine the depression.

According to one embodiment of the present invention, many users in their 20s and 30s can also receive diagnoses of their depression without feeling uncomfortable.

According to one embodiment of the present invention, a large number of people can be diagnosed on whether depression is present through a kind of telemedicine concept, and the diagnosis can be performed at separate times between patients and doctors rather than performed in real time after each doctor precisely sets the time with the patient or user.

According to one embodiment of the present invention, the medical staff can quickly check only the important parts selected by the machine learning model without playing the entire video by the medical staff.

According to one embodiment of the present invention, the parts determined as important by the machine learning model are automatically extracted, so that the videos can be checked in an efficient user interface.

In one embodiment of the present invention, voice features, facial expressions, and text are entirely determined in a multi-modal manner, so that a comprehensive determination on symptoms of depression can be provided.

In one embodiment of the present invention, information on the determination basis or explanation of the machine learning model is provided to the medical staff, rather than simply providing determination results of the machine learning model, so that the medical staff can quickly determine whether to accept the opinion.

An embodiment of the present invention may be implemented in the form of a recording medium including instructions executable by a computer, such as program modules executed by a computer. Computer readable media can be any available media that can be accessed by a computer and includes both volatile and nonvolatile media, removable and non-removable media. Also, computer readable media may include both computer storage media and communication media. Computer storage media includes both volatile and nonvolatile, removable and non-removable media implemented in any method or technology for storage of information such as computer readable instructions, data structures, program modules or other data. Communication media typically includes computer readable instructions, data structures, program modules, or other data in a modulated data signal such as a carrier wave, or other transport mechanism, and includes any information delivery media.

Although the methods and systems of the present invention have been described with reference to specific embodiments, some or all of their components or operations may be implemented using a computer system having a general-purpose hardware architecture.

Although the above embodiments have been described with reference to the limited embodiments and drawings, however, it will be understood by those skilled in the art that various changes and modifications may be made from the above-mentioned description. For example, even though the described descriptions may be performed in an order different from the described manner, and/or the described components such as system, structure, device, and circuit may be coupled or combined in a form different from the described manner, or replaced or substituted by other components or equivalents, appropriate results may be achieved.

Therefore, other implementations, other embodiments, and equivalents to the claims are also within the scope of the following claims.

The invention claimed is:

1. A method for providing depression preliminary diagnosis information by using a machine learning model performed on a computing device having at least one processor and at least one memory, the method comprising:

deriving the depression preliminary diagnosis information by using a machine-learned model for at least one answer video captured using a camera and a microphone in a patient terminal; and providing the depression preliminary diagnosis information to a user, wherein the machine-learned model outputs, for each of a plurality of sections of the answer video, a degree of depression, wherein a first display screen displayed by the providing the depression preliminary diagnosis information to the user includes:

an answer video layer for displaying the answer video;

a script layer for displaying question information related to the answer video and answer text information extracted from the answer video; and a depression graph layer for displaying the degree of depression output according to a time axis, wherein the depression graph layer includes:

a first reference display element for indicating that the degree of depression exceeds a predetermined first reference and a second reference display element indicating that the degree of depression exceeds a predetermined second reference higher than the predetermined first reference, and wherein a video time point of the answer video layer is changeable to a time point corresponding to a position of a script part selected according to an input by the user in the script layer, and the video time point of the answer video layer is changeable to a time point corresponding to a position on the time axis selected according to an input by the user in the depression graph layer;

wherein the deriving includes:

extracting multiple words, multiple image frames, and multiple pieces of voice information extracted from text of a voice from the answer video;

deriving multiple pieces of first feature information from the words, multiple pieces of second feature information from the image frames, and multiple pieces of third feature information from the pieces of voice information by using each detailed machine learning model or algorithm; and deriving derived information including the degree of depression by using an artificial neural network considering sequence data from the pieces of first feature information, the pieces of second feature information, and the pieces of third feature information.

2. The method of claim 1, wherein the diagnosing includes deriving the depression preliminary diagnosis information by using the machine-learned model from the answer video, based on multiple words extracted from text of a voice, multiple image frames corresponding to the words, respectively, and multiple pieces of voice information corresponding to the words, respectively.

3. The method of claim 1, wherein the diagnosing includes:

deriving the depression preliminary diagnosis information by using the machine-learned model, based on at least two pieces of information among multiple words, multiple image frames, and voice information extracted from text of voice extracted from the answer video.

4. The method claim 1, wherein the artificial neural network considering the sequence data corresponds to a recurrent neural network or a transformer-based machine learning model based on an attention mechanism, and the first feature information, the second feature information, and the third feature information corresponding to each of the words are input, in a merged form, to the recurrent neural network or the transformer-based machine learning model.

5. The method of claim 1, wherein a part of the answer text displayed on the script layer is displayed with change in at least one of highlight, font, size, color, and underline according to at least one of the degree of depression and a type of depression in the depression preliminary diagnosis information corresponding to the part of the answer text.

6. The method of claim 5, wherein the part of the answer text displayed with the change in at least one of the highlight, font, size, color, and underline corresponds to a condition that the degree of depression of the depression preliminary diagnosis information corresponding to the part of the answer text is equal to or greater than a predetermined reference, and the video time point of the answer video layer is changed to a time point corresponding to a position of the part of the answer text when the user selects the part of the answer text displayed with the change in at least one of the highlight, font, size, color, and underline.

7. The method of claim 1, wherein the first reference display element indicates a detailed type of the depression.

8. The method of claim 1, wherein the first display screen further includes a scroll layer for displaying scroll information of the script layer, the scroll layer displays an information display element at each time point displayed according to at least one of the degree of depression and a type of depression in the depression preliminary diagnosis information, and the time point is shifted to a position of answer text corresponding to the selected information display element in the script layer when the user selects the information display element.

9. The method of claim 1, wherein a second display screen displayed by the providing the depression preliminary diagnosis information to the user includes:

the answer video layer for displaying the answer video; and a summary script layer for displaying summary answer text information extracted from the answer video, and wherein the summary answer text information includes at least one part of the answer text in which the degree of depression in the depression preliminary diagnosis information corresponding to the part of the answer text is equal to or greater than a predetermined reference, and the video time point of the answer video layer is changeable to a time point corresponding to a position of a script part selected according to an input by the user in the summary script layer.

10. The method of claim 9, wherein the second display screen further includes at least one selection input element corresponding to each of the summary answer text information, and a part of an answer video corresponding to a part of the selection input element or the summary answer text information selected according to an input of the user is played.

11. A device for providing depression preliminary diagnosis information by using a machine learning model implemented as a computing device having at least one processor and at least one memory, the device comprising:

a diagnosing unit for deriving the depression preliminary diagnosis information by using a machine-learned model for at least one answer video captured using a camera and a microphone in a patient terminal; and a providing unit for providing the depression preliminary diagnosis information to a user, wherein the machine-learned model outputs, for each of a plurality of sections of the answer video, a degree of depression, wherein a first display screen displayed by the providing the depression preliminary diagnosis information to the user includes:

an answer video layer for displaying the answer video;

a script layer for displaying question information related to the answer video and answer text information extracted from the answer video; and a depression graph layer for displaying the degree of depression output according to a time axis, wherein the depression graph layer includes:

a first reference display element for indicating that the degree of depression exceeds a predetermined first reference; and a second reference display element indicating that the degree of depression exceeds a predetermined second reference higher than the predetermined first reference, and wherein a video time point of the answer video layer is changeable to a time point corresponding to a position of a script part selected according to an input by the user in the script layer, and the video time point of the answer video layer is changeable to a time point corresponding to a position on the time axis selected according to an input by the user in the depression graph layer;

wherein the deriving includes:

extracting multiple words, multiple image frames, and multiple pieces of voice information extracted from text of a voice from the answer video;

deriving multiple pieces of first feature information from the words, multiple pieces of second feature information from the image frames, and multiple pieces of third feature information from the pieces of voice information by using each detailed machine learning model or algorithm; and deriving derived information including the degree of depression by using an artificial neural network considering sequence data from the pieces of first feature information, the pieces of second feature information, and the pieces of third feature information.

12. A non-transitory computer-readable medium recording program instructions for implementing a method for providing depression preliminary diagnosis information by using a machine learning model performed on a computing device having at least one processor and at least one memory, wherein the method comprising:

deriving the depression preliminary diagnosis information by using a machine-learned model for at least one answer video captured using a camera and a microphone in a patient terminal; and providing the depression preliminary diagnosis information to a user, wherein the machine-learned model outputs, for each of a plurality of sections of the answer video, a degree of depression, wherein a first display screen displayed by the providing the depression preliminary diagnosis information to the user includes:

an answer video layer for displaying the answer video;

a script layer for displaying question information related to the answer video and answer text information extracted from the answer video; and a depression graph layer for displaying the degree of depression output according to a time axis, wherein the depression graph layer includes:

a first reference display element for indicating that the degree of depression exceeds a predetermined first reference; and a second reference display element indicating that the degree of depression exceeds a predetermined second reference higher than the predetermined first reference, and wherein a video time point of the answer video layer is changeable to a time point corresponding to a position of a script part selected according to an input by the user in the script layer, and the video time point of the answer video layer is changeable to a time point corresponding to a position on the time axis selected according to an input by the user in the depression graph layer;

wherein the deriving includes:

extracting multiple words, multiple image frames, and multiple pieces of voice information extracted from text of a voice from the answer video;

deriving multiple pieces of first feature information from the words, multiple pieces of second feature information from the image frames, and multiple pieces of third feature information from the pieces of voice information by using each detailed machine learning model or algorithm; and deriving derived information including the degree of depression by using an artificial neural network considering sequence data from the pieces of first feature information, the pieces of second feature information, and the pieces of third feature information.

* * * * *